United States Patent [19]

Ascer et al.

[11] Patent Number: 4,585,010
[45] Date of Patent: Apr. 29, 1986

[54] PROCESS AND APPARATUS FOR MEASUREMENT OF OUTFLOW RESISTANCE

[76] Inventors: Enrico Ascer, 231 Delhi Rd., Scarsdale, N.Y. 10583; Lee M. E. Morin, Room 334 UOPH Box 18 Subase, Groton, Conn. 06349; Frank J. Veith, 3184 Grand Concourse, Bronx, N.Y. 10458

[21] Appl. No.: 627,065

[22] Filed: Jul. 2, 1984

[51] Int. Cl.$^4$ ............................................. A61B 5/02
[52] U.S. Cl. .................................. 128/673; 128/692; 128/748; 604/175
[58] Field of Search ............................... 128/691–693, 128/672–673, 668; 604/96–100, 175

[56] References Cited

U.S. PATENT DOCUMENTS

| | | | |
|---|---|---|---|
| 3,124,132 | 3/1964 | Sullivan et al. | 128/675 |
| 3,240,207 | 3/1966 | Barker et al. | 128/675 |
| 3,310,051 | 3/1967 | Schulte | 604/175 |
| 3,625,199 | 12/1971 | Summers | 128/748 |
| 4,190,057 | 2/1980 | Hill et al. | 128/672 X |

FOREIGN PATENT DOCUMENTS 0833198  6/1981  U.S.S.R. ................................ 128/691

Primary Examiner—Kyle L. Howell
Assistant Examiner—Angela D. Sykes
Attorney, Agent, or Firm—Ostrolenk, Faber, Gerb & Soffen

[57] ABSTRACT

A method and apparatus is disclosed for determining the likelihood of success of a bypass graft. One end of the graft is first fixed to the vessel which is to be bypassed. Alternatively, a double lumen balloon tip catheter is inserted into the vessel. A fixed amount of heparinized normal saline is then applied to the proximal end of the graft or catheter and into the vessel. The pressure within the graft vessel is measured and integrated over a given time and the volume of the saline which flows during that time is divided into the integrated pressure to produce a measure of the outflow bed resistance. The proximal side of the vessel is clamped in order to measure distal run-off bed or outflow resistance. A measurement of greater than 1.2 millimeters of mercury per milliliter of injected fluid per minute predicts that the grafts are likely to be unsuccessful.

13 Claims, 6 Drawing Figures

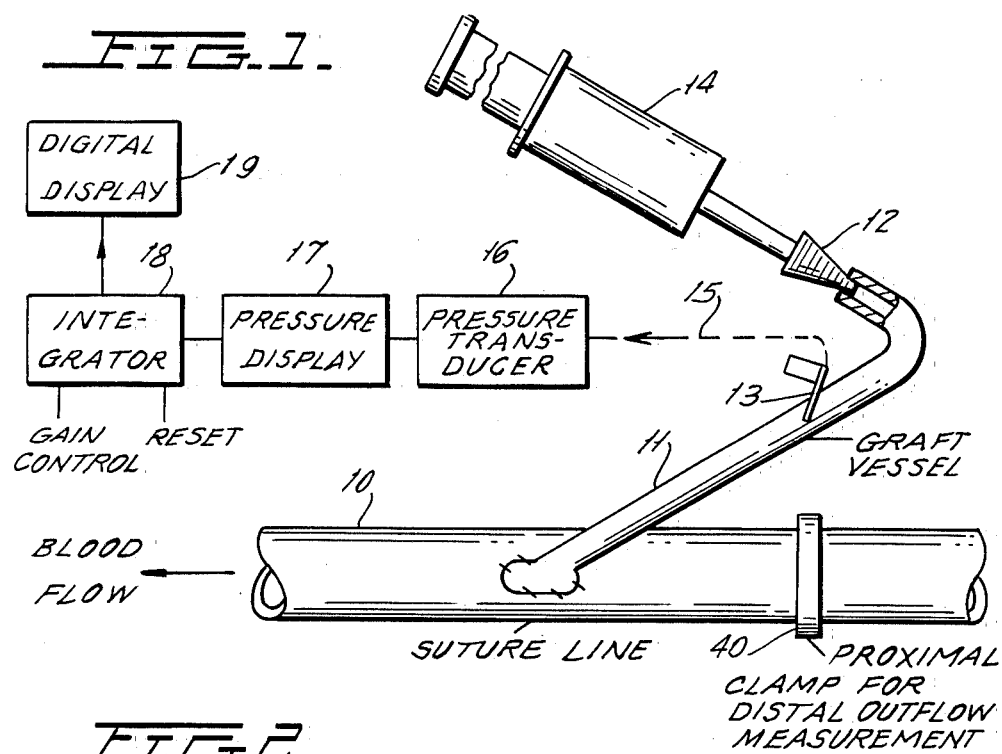
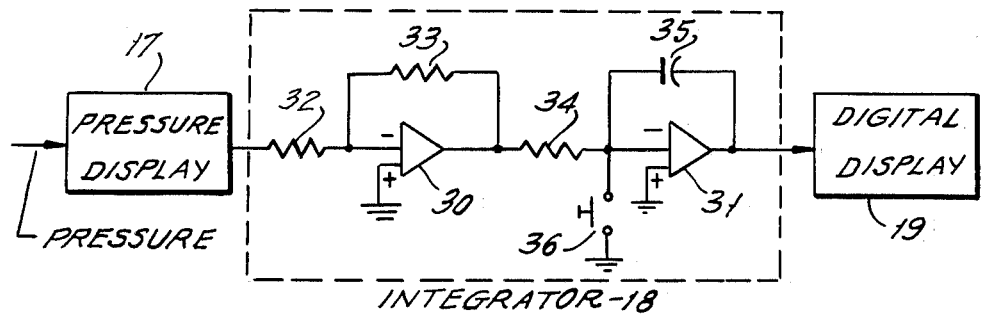
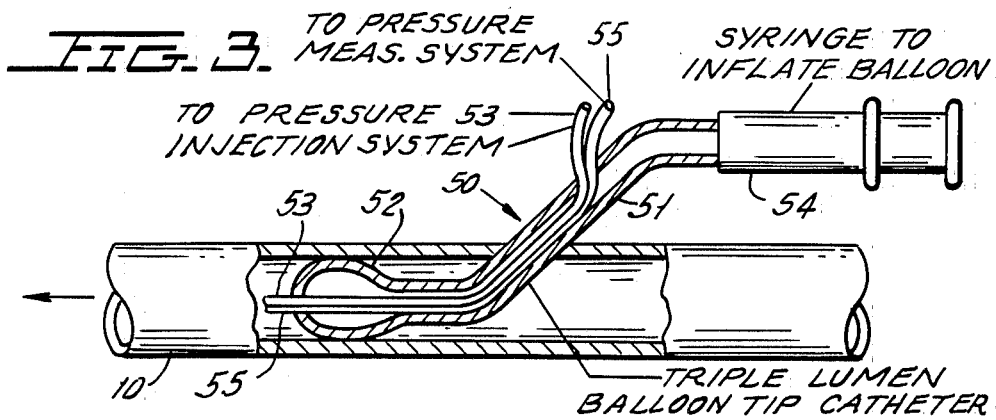

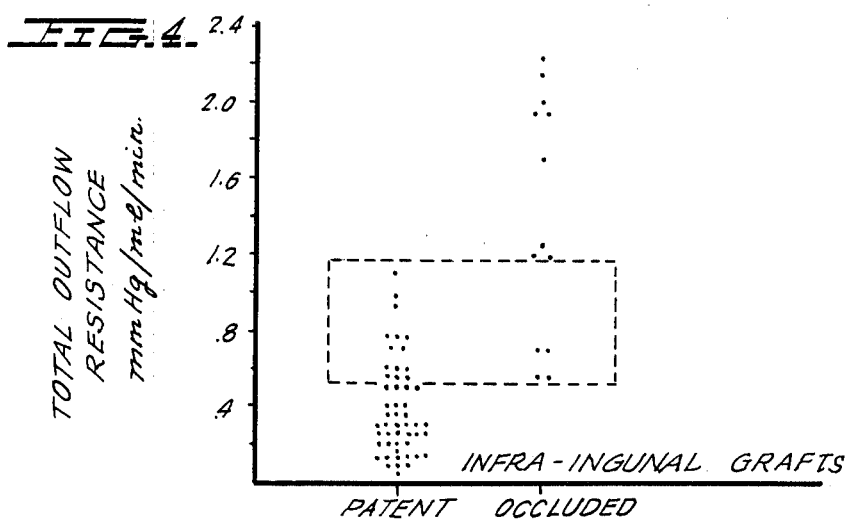
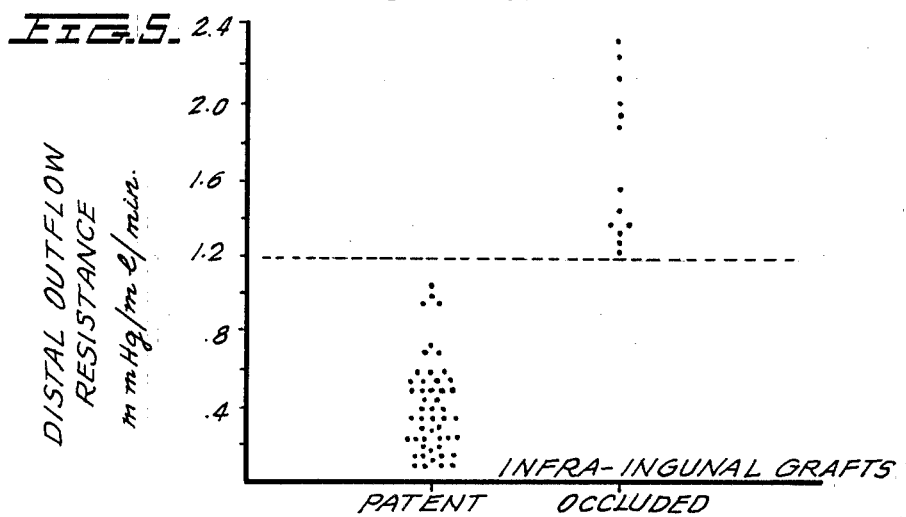
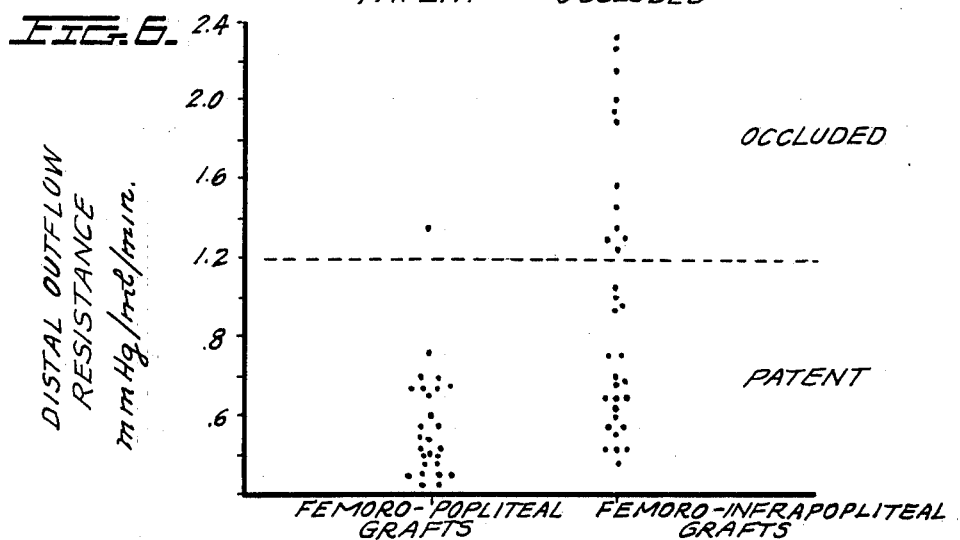

PROCESS AND APPARATUS FOR MEASUREMENT OF OUTFLOW RESISTANCE

BACKGROUND OF THE INVENTION

This invention relates to a process and apparatus for predicting the likelihood of success of a bypass, particularly in infrainguinal arterial reconstructions for treating severe limb ischemia.

Infrainguinal arterial reconstructions are well-established modalities for treating severe limb ischemia. However, bypass failures occur in many cases, particularly after reconstructions to infrapopliteal vessels. Because of this, a reliable predictor of bypass graft failure has been sought over the last two decades as a means for excluding patients from attempts or repeated attempts at revascularization. Various preoperative criteria, including arteriographic evaluation of the runoff bed and hemodynamic and clinical assessment of the degree of ischemia, have proven to be unreliable prognostic indices of graft outcome. Furthermore, intraoperative measurement of femoropopliteal bypass graft flow rates and outflow tract resistance have proven to be inconsistent predictors of graft patency.

Previous attempts to predict failure by assessing outflow tract resistance have been unsuccessful because the early and late failure of infrainguinal bypass grafts may be due to many factors other than this parameter. One confusing factor with the early studies is that all were performed on femoropopliteal bypasses in which outflow tract resistance was only rarely high enough that it alone would cause a failure. No comparable information, however, was available for bypasses to infrapopliteal vessels.

It is generally believed by vascular surgeons that poor graft outflow with high outflow resistance is an important cause of early graft failure. However, the techniques available for measurement of outflow resistance were generally unsatisfactory and could not serve as a predictor of the graft failure. Moreover, because of the rarity of early failures in femoropopliteal bypasses, even with bypass insertions into isolated popliteal artery segments, the outflow resistance measurement was of no discriminate value in predicting early failure of this operation.

BRIEF DESCRIPTION OF THE INVENTION

In accordance with the present invention, a novel process and apparatus is disclosed for measurement of the runoff bed or outflow resistance of a blood carrying vessel which is to be subjected to a graft. The invention also includes the discovery that graft patency is likely when the runoff bed resistance as measured by the ratio of the integrated pressure of a fluid injected into the graft over a given time, to the volume of the fluid inserted during that time, is less than about 1.2 units. This measure was particularly accurate when distal outflow resistance is measured. The novel invention and critical outflow bed resistance value as a predictor for graft patency applies particularly to bypasses of infrapopliteal arteries.

In carrying out the invention in its preferred form, one end of a graft vessel is attached to the vessel which is to be bypassed. A source of heparinized saline fluid is then injected into the free end of the graft vessel and a volume of the fluid is placed under pressure such that it flows through the graft vessel into the vessel to be bypassed. Approximately 5 to 15 milliliters of fluid is initially permitted to flow before measurements are made. This permits the runoff bed system to conform to the increased pressure, thereby removing any compliance variables from the later measurement. Thereafter, during a measurement interval, the fluid remains pressurized and its pressure is integrated for a given length of time. The volume of fluid which flows during that length of time is divided into the integrated pressure to yield a runoff bed resistance measurement. A total of about 20-50 milliliters of fluid is injected during the procedure at pressures which may vary from about 30 to about 60 milliliters of mercury. The integrated pressure may be displayed on a digital display, if desired.

While the invention described above has been carried out during the intraoperative procedure and after one end of the graft is attached to the vessel to be bypassed, it is also possible to employ a triple lumen balloon-tip catheter which is inserted into the vessel to be bypassed. The outer balloon tip is inflated to serve as a proximal clamp and the resistance measuring system described above can be connected to the central lumen which injects fluid through the second and measures its pressure through the third and processes the pressure and volume variables as described above. This latter system can be employed during angiography procedures.

BRIEF DESCRIPTION OF THE DRAWINGS

FIG. 1 schematically illustrates the invention as applied to a vessel which is to be bypassed, after one end of the graft vessel is attached thereto.

FIG. 2 is a circuit diagram of the integrator circuit of FIG. 1.

FIG. 3 schematically illustrates the manner in which a double lumen balloon-tip catheter can be employed for carrying out the invention during an angiography procedure.

FIG. 4 shows the total outflow resistance obtained with 64 infra-inguinal grafts on 59 patients with the line of dots above the label "patent" showing successful grafts and the line of dots above the label "occluded" showing unsuccessful grafts.

FIG. 5 is a chart similar to FIG. 4 but displays the results as a function of measured distal outflow resistance.

FIG. 6 breaks down the results of FIG. 5 between femoro-popliteal grafts and femoro-infrapopliteal grafts.

DETAILED DESCRIPTION OF THE INVENTION

Referring first to FIG. 1, there is shown therein a blood vessel such as the vessel 10 which must be bypassed for example to treat severe limb ischemia or which may be a coronary artery or the like. In carrying out the invention, a graft vessel 11 has one end thereof sutured to the vessel 10 so that the two communicate. When forming the graft, the vessel 10 is clamped both proximal and distal to the graft site. When making the subsequent resistance measurement to be described, either both clamps or only one of the clamps is removed. Vessel 11 may be a polytetrafluoroethylene vessel or an autogenous saphenous vein graft.

The distal end of the graft vessel 11 is connected to a conventional "Christmas tree" 12. The Christmas tree 12 is connected to a syringe 14 which is a source of heparinized saline fluid which can be injected into the graft vessel 11. A #23 gauge "butterfly" needle 13 is placed through the wall of the graft vessel at a site which will be trimmed off at a later stage of the surgery.

The #23 gauge "butterfly" needle 13 has an output tube 15 which is connected to a pressure transducer 16. The pressure transducer 16 can, for example, be a standard pressure transducer manufactured, such as a Gould-Statham Model 23 ID. The output of the pressure transducer 16 is then connected to a pressure display 17 which can, for example, be a EKG-blood pressure monitor such as the Datascope model 870.

The output of the pressure display unit 17 is then connected to a pressure integrator unit 18 which will be later described in FIG. 2. The integrator output is connected to a digital display 19 which can be a Datascope model P3 digital display.

The integrator circuit 18 is shown in FIG. 2 and consists of two high performance 741 type operational amplifiers 30 and 31 interconnected as shown. The input to amplifier 30 consists of a 10 kilohm resistor 32. A 10 kilohm bypass resistor 33 is also provided. The output of the operational amplifier 30 is coupled to the input of operational amplifier 31 through a 1 megohm resistor 34. A 10 microfarad, very low leakage capacitor 35 is connected in parallel with the operational amplifier 31. A pushbutton contact 36 is also provided to ground the input to the operational amplifier 31 in order to reset the integrator 18 to a zero value for a new integration operation. A suitable power supply (not shown) which can, for example, consist of eight AA alkaline batteries which provide six volts for the operational amplifiers may also be provided (not shown). By employing a low leakage capacitor 35 for the integrator circuit, the integration operation will be stable over several minutes.

The input signal to the pressure display 17 from the pressure transducer of FIG. 1 can, for example, be approximately 1 volt which corresponds to 100 millimeters of mercury, while the output to the digital display 19 in FIG. 2 can be about 1 volt, which corresponds to 1,000 millimeters of mercury-seconds.

In operation of the systems of FIGS. 1 and 2, approximately 5 to 15 milliliters of saline is initially injected by depression of the plunger of syringe 14. No measurement is made during this time so that the runoff bed can comply to the change in pressure without producing compliance variables. Thereafter, additional fluid is injected for a given time and the pressure produced by this fluid is measured in the pressure transducer 16 over that time period, and the volume injected during the time period is also noted. The pressure is displayed in the display 17 and integrated in the integrator 18 and ultimately is displayed in the digital display 19. The total pressure integral, divided by the actual volume injected during the integration time period is equal to the runoff bed resistance and becomes a predictor of the success of the ultimate graft.

It has been found that this predictor is even more accurate when the distal runoff bed resistance is measured. The distal runoff bed resistance can be measured by clamping off the vessel 10 at the proximal side of the graft by the proximal clamp 40. It may also be useful to measure the proximal runoff bed resistance, this being obtained by clamping the distal side of vessel 10 during the runoff bed resistance measurement.

FIG. 3 shows a second embodiment of the invention, wherein the resistance measurement can be made, for example, during an angiography process. In accordance with the arrangement of FIG. 3, a triple lumen balloon-tip catheter 50 is employed which has an outer tube 51 which terminates in an inflatable balloon section 52. Two internal hollow elongagted tubes 53 and 55 extend through and are sealed to the end of the balloon tip catheter. The outer conduit 51 is connected to a syringe 54 which is operable to inflate the balloon end 52. The conduit 53 penetrates the conduit 51 in a sealed manner and is connectable to a source of contrast fluid for the angiography procedure, and/or the fluid injecting equipment of FIG. 1 in the manner in which the graft vessel 11 of FIG. 1 was connected thereto. The conduit 55 penetrates the conduit 51 in a sealed manner and is connectable to the pressure measuring equipment of FIG. 1 in the manner in which the "butterfly" needle 13 of FIG. 1 was connected thereto.

When employed in the manner of FIG. 3, the invention has a broader field of applicability and can, for example, measure the quantity of an agent which is injected into an artery to lyse clots such as streptokinase or urokinase and measuring the vessel resistance during angiography. Thus, prior to surgery, the catheter 50 can be placed in the vessel percutaneously and an X-ray contrast material can be injected thrugh the conduit 53 to define the runoff and anatomy. In certain circumstances an attempt may be made to scrape the interior of the artery; this process being known as angioplasty.

By using the balloon-tipped catheter 51, the distal resistance can be measured in the artery at the time of the angiography by inflating the balloon 52 before the resistance measure is made. This procedure can be carried out before surgery or to decide whether or not to inject clot lysing agents. Obviously, resistance in the artery proximal to the graft site can also be measured if desired.

It is now possible to describe the clinical methods and results which were obtained when using the present invention for the measurement of outflow resistance and for predicting the patency of grafts. These results were obtained in procedures carried out by the Division of Vascular Surgery, Montefiore Medical Center, Albert Einstein College of Medicine, New York, N.Y.

Intraoperative outflow resistance measurements were obtained during 64 infrainguinal arterial reconstructions for limb salvage in 59 patients at the Montefiore Medical Center. There were 30 males and 29 females, ranging in age from 51 to 87, with a mean of 68 years. Cardiovascular risk factors were common and often multiple. The indications for surgery were rest pain in 14 patients (22%), nonhealing ischemic ulcer in 23 (36%) and gangrene in 27 (42%). There were 31 femoropoliteal (F-P) bypasses and 33 bypasses to infrapopliteal arteries (F-D). Expanded polytetrafluoroethylene (PTFE) grafts were used in 42 instances (25 F-P; 17 F-D), while autogenous saphenous vein grafts were used in the remaining 22 bypasses (6 F-P; 16 F-D). Only veins larger than 3.5 mm and 4 mm in diameter were used for F-D and F-P bypasses, respectively. Six mm PTFE grafts were used for all F-P bypasses and tapered 6.5 to 4.5 mm for all F-D bypasses.

Of the 31 F-P bypasses, 16 were to the below-knee popliteal artery, while 15 were inserted above the knee. Of the 33 F-D bypasses, 9 were to the anterior tibial, 6 to the posterior tibial, 9 to the peroneal and 9 to the dorsalis pedis arteries. Sixteen of the F-P bypasses were inserted into an isolated popliteal artery segment. Fourteen of the F-D bypasses were performed with an intact pedal arch and 19 were performed when the pedal arch was either incomplete or absent on preoperative and/or intraoperative angiography.

All operations were performed under light general anesthesia with continuous monitoring of the systemic blood pressure via a radial artery catheter. For particularly high risk patients, a entral venous line was inserted, and whenever indicatd, a ballon-tipped catheter was placed in the pulmonary artery for measurement of left ventricular function. Meticulous care was taken in construction of all anastomoses which were performed with continuous 6-0 polypropylene sutures. All patients were observed for at least three months after their operation.

After completion of the distal anastomosis of the bypass, 20–50 ml of normal saline was injected with a syringe into the fluid-filled graft and allowed to flow into the bypass outflow bed. During this injection, the pressure generated in the graft was measured and electrically integrated, as disclosed previously. This pressure integral was a function of the outflow bed resistance which can be quantitated by the application of the hydraulic analog of Ohm's law to the arterial system:

$$P = R \cdot F$$

where P=pressure (mmHg), R=resistance (mmHg/ml/min) and F=flow (ml/min).

Assuming the resistance to be constant during the fluid injection, the integration of both sides of this equation can be expressed as $$\int_0^t P \, dt = R \int_0^t F \, dt$$

Since, by definition, the integral of flow $$\left( \int_0^t F \, dt \right)$$

is the volume (V) injected, the resistance is:

$$R = \int_0^t \frac{P \, dt}{V}$$

Thus, this equation permits the determination of resistance by measuring the integral of pressure and the volume injected.

The pressure generated during injection was integrated as described in FIGS. 1 and 2. The graft was clamped proximally and a 23-gauge butterfly needle inserted into the lumen of the graft and connected to the transducer by polyethylene tubing. To avoid interference of back pressure generated from collateral flow, calibration of this pressure to zero was done before starting to integrate the pressure generated by the saline injection through the graft. If the back pressure is pulsatile, calibration of the mean pressure to zero is performed. To minimize the arterial and graft compliance variables, the pressure integration is started only after 5–15 ml of saline has been injected, by which time a pressure plateau has been reached as displayed on the Datascope 17. This plateau corresponds to an injection pressure which is arbitrarily placed in the range of 30–50 mmHg for femoropopliteal bypasses and 40–60 mmHg for infrapopliteal bypasses.

Measurements by this technique were performed during 64 infrainguinal arterial reconstructions with the proximal and distal segments of the recipient artery unclamped (total outflow resistance), with the proximal segment clamped (distal outflow resistance) and, finally, with the distal segment clamped (proximal outflow resistance).

Angiographic visualization of the inflow and outflow tracts was obtained preoperatively in all cases. In addition, completion arteriograms were routinely performed intraoperatively to verify the absence of defects at the distal anastomosis and, in some instances, to define more clearly the morphologic characteristics of the outflow bed.

The outflow resistance measurements obtained with both segments of the recipient artery unclamped (total outflow) showed a good correlation with graft patency as shown in FIG. 4. In FIG. 4, all grafts with a total outflow resistance equal to or above 1.1 units thrombosed within the first three post-operative months, and all grafts with a total outflow resistance below 0.5 unit remained patent. Grafts with a total outflow resistance between 0.5 and 1.1 units had some failures and some successes. This overlap prevents this measurement from being a perfect predictor of graft patency. However, when outflow resistance was measured with the proximal recipient arterial segment clamped (distal outflow resistance), a more accurate predictor of success or failure was obtained. Thus, all bypasses with outflow resistances equal to or greater than 1.2 units occluded, and all bypasses with values below 1.2 units remained patent, as shown in FIG. 5.

Only 1 (3%) of the 31 femoropopliteal grafts occluded as shown in FIG. 6. The occluded femoropopliteal graft had the highest measured distal outflow resistance (1.38 units). The remaining femoropopliteal bypasses had a mean distal outflow resistance of 0.36 units, with a range of 0.08 to 0.74 unit (FIG. 6).

Of the 33 F-D grafts, 12 (36%) occluded and 2 (64%) remained patent as shown in FIG. 6. Analysis of several variables which may predict graft outcome was possible for this group. These included type of graft material (autogenous saphenous vein, PTFE), presence or absence of intact pedal arch, preoperative ABPI equal to or less than 0.4 or greater than 0.4, preoperative PVR amplitude equal to or less than 4 mm or greater than 4 mm and presence or absence of arterial calcification. None of these variables proved to be a statistically significant (fisher's Exact test) predictor of early graft patency or thrombosis. However, distal outflow resistance was such a predictor. When this measurement was less than 1.2 units, all grafts remained patent, and values of 1.2 units or more were invariably associated with graft occlusion. This difference was statistically significant by the Fisher's Exact test.

Of the 13 occluded grafts in this series, 8 had a simple thrombectomy which was uniformly followed by reocclusion in the immediate post-operative period. Three grafts were not reoperated upon and the remaining were treated by thrombectomy and graft extension to a more distal artery in one patient and to a different leg artery in the other. Both of these extended grafts remained patent over three months.

From the above, it is seen that high outflow resistance is an important cause of early graft failure. The present invention provides a simple, rapid, reproducible method for quantitating the outflow resistance of a bypass. Because of the rarity of early failures in femoropopliteal bypasses, even with bypass insertions into isolated popliteal artery segments, this outflow resistance measurement is of no discriminate value in predicting early failure of this operation. However, in bypasses to infrapopliteal arteries, high outflow resistance has a strongly positive correlation with early graft occlusion. When the total outflow resistance measurement was modified by occluding the proximal outflow from the graft so that only the distal outflow resistance was measured, the method provided a highly accurate index of failure and success. All infrapopliteal bypasses with distal outflow resistances of 1.2 units or more thrombosed in the early post-operative period, while all bypasses with lower resistances remained patent at least three months.

It is of interest that the measurements of bypass outflow resistance failed to correlate with other preoperative hemodynamic and angiographic parameters, some of which have been thought to indicate a "poor" or "high resistance" outflow bed and to contraindicate attempts at arterial revascularization. The poor correlation of measured outflow resistance with these parameters may explain why they have been disappointing predictors of bypass outcome.

A disadvantage of the method of the invention for measuring outflow resistance shown in FIGS. 1 and 2 is that it can only be used during operation and, therefore, cannot serve to exclude patients from attempts at revascularization procedures. However, high resistance measurements determined at operation can exclude patients from hopeless attempts at reoperation for thrombosis. More importantly, the intraoperative observation of a high bypass outflow resistance in or near the certain failure range (i.e. over 1.2 units) can be used as an indication to perform some form of bypass revision to decrease outflow resistance. This can be accomplished by adding a graft extension to another infrapopliteal artery as a sequential bypass.

Another potential problem with the present method relates to the fact that resistance in the outflow bed may not be constant and may vary with the rate of saline injection and the pressure generated. It has been found, however, that resistance remains virtually constant when the pressure increment generated by the injection is kept between 30 and 60 mmHg. Accordingly, all measurements were made with injection pressures within this range.

Although the present invention has been described in connection with a number of preferred embodiments thereof, many variations and modifications will now become apparent to those skilled in the art. It is preferred, therefore, that the pesent invention be limited not by the specific disclosure herein, but only by the appended claims.

What is claimed is:

1. A process for measuring the resistance to flow in the runoff bed of a blood carrying vessel comprising the steps of attaching one end of a bypass graft vessel to said blood carrying vessel so that the interior of said bypass graft vessel communicates with said blood carrying vessel; injecting a volume of a substantially incompressible fluid into said bypass graft vessel so that said fluid flows into said blood carrying vessel; measuring the pressure at which said fluid is injected into said bypass graft vessel for a given time; integrating said pressure which is measured during said given time; measuring the volume of fluid which flows during said given time, and dividing said integrated pressure by said measured volume to determine resistance to flow in the runoff bed.

2. The process of claim 1, wherein said blood carrying vessel is unclamped both proximal and distal of the point of attachment of said blood carrying vessel to said bypass graft vessel.

3. The process of claim 1, wherein said blood carrying vessel is clamped proximally of the point of attachment to said bypass graft vessel before injection of said fluid.

4. The process of claim 1, 2 or 3, wherein said fluid is a saline solution and said measured volume is from about 20 to about 50 milliliters.

5. The process of claim 4, wherein said pressure at which said fluid is injected is approximately 30 to 60 millimeters of mercury.

6. The process of claim 5, wherein about 5 to 15 milliliters of said fluid are initially injected before the measurement of pressure integral divided by volume is made, in order to eliminate compliance variables from said measurement.

7. The process of claim 1, 2 or 3, wherein said pressure at which said fluid is injected is between about 30 to about 60 millimeters of mercury.

8. The process of claim 1, 2, or 3, wherein about 5 to 15 milliliters of said fluid are initially injected before the measurement of pressure integral divided by volume is made, in order to eliminate compliance variables from said measurement.

9. A process for determining graft patency, comprising the forming of the distal anastomosis of a bypass graft, injecting a fluid into the free end of said bypass graft and measuring the runoff bed resistance to flow of said fluid, and determining whether said resistance is greater than or less than 1.2 millimeters of mercury per milliliter per minute, whereby a measurement greater than 1.2 millimeters of mercury per milliliter per minute is an indication of a low probability of success for the graft.

10. The process of claim 9, wherein said resistance is measured by integrating the pressure of said fluid over a given time and dividing the integral of pressure so obtained by the volume of fluid injected during said given time.

11. The process of claim 10, wherein from 20 to 50 milliliters of fluid are injected at a pressure from 30 to 60 millimeters of mercury.

12. The process of claim 11, wherein 5 to 15 milliliters of said fluid are initially injected before said measurement is made.

13. Apparatus for measuring runoff bed resistance to determine the patency of a graft to be made to a blood carrying vessel; said apparatus comprising a source of fluid under pressure; means for connecting said source of fluid to said blood carrying vessel; pressure monitor means for measuring the instantaneous pressure of said fluid; volume monitor means for measuring the volume of said fluid which is injected into said vessel; and integrating means for integrating said instantaneous pressure for a given length of time, whereby the ratio of integrated pressure measured by said means for integrating to the volume of fluid injected during said given length of time is equal to said runoff bed resistance.

* * * * *